United States Patent [19]

Kellett et al.

[11] Patent Number: 5,034,222
[45] Date of Patent: Jul. 23, 1991

[54] COMPOSITE GEL-FOAM AIR FRESHENER

[75] Inventors: George W. Kellett, Cranford, N.J.; James A. Smith, Chatham, Mass.; Bonnie Johanning, Clifton, N.J.

[73] Assignee: Creative Products Resource Associates, Ltd., Clifton, N.J.

[21] Appl. No.: 487,208

[22] Filed: Mar. 1, 1990

[51] Int. Cl.$^5$ .............................................. A61L 9/04
[52] U.S. Cl. ...................... 424/76.4; 424/76.3; 239/55; 252/174.11; 252/315.1; 514/944; 514/945; 521/53; 521/55; 523/102
[58] Field of Search ............................ 424/76.4, 76.3; 523/102; 514/944, 945; 239/55-60; 252/174.11, 315.1; 521/53, 55

[56] References Cited

U.S. PATENT DOCUMENTS

| | | | |
|---|---|---|---|
| 2,927,055 | 3/1960 | Lanzet | 167/42 |
| 3,730,434 | 5/1973 | Engel | 239/47 |
| 3,969,280 | 7/1976 | Sayce et al. | 252/522 |
| 3,997,480 | 12/1976 | Singleton et al. | 252/522 |
| 4,056,612 | 11/1977 | Lin | 424/76 |
| 4,117,110 | 9/1978 | Hautmann | 424/76 |
| 4,178,264 | 12/1979 | Streit et al. | 252/316 |
| 4,226,944 | 10/1980 | Stone | 521/76 |
| 4,309,509 | 1/1982 | Wood | 531/132 |
| 4,339,550 | 7/1982 | Palinczar et al. | 521/99 |
| 4,563,483 | 1/1986 | Smith et al. | 521/111 |
| 4,581,385 | 4/1986 | Smith et al. | 521/111 |
| 4,594,362 | 6/1986 | Smith et al. | 521/52 |
| 4,719,040 | 1/1988 | Traas et al. | 512/4 |
| 4,735,626 | 4/1988 | Smith | 8/137 |
| 4,755,377 | 7/1988 | Steer | 424/76.4 |

FOREIGN PATENT DOCUMENTS 1241914 8/1971 United Kingdom .
1598449 9/1981 United Kingdom .

Primary Examiner—Thurman Page
Assistant Examiner—D. Gabrielle Phelan
Attorney, Agent, or Firm—Merchant, Gould, Smith, Edell, Welter & Schmidt

[57] ABSTRACT

A solid composite air freshening article is provided which comprises a granular foam phase dispersed throughout a gelled phase in an amount effective to provide a sustained release of an effective amount of volatile air freshening ingredients present in both the foam and gelled phases. The foam phase comprises granules of a hydrophilic, polyurethane foam incorporating a volatile air freshening ingredient, a surfactant, and a solid filler material, while the gelled phase comprises water, a gelling agent, an organic solvent, and the same or a different air freshening ingredient as the granular foam phase.

24 Claims, 1 Drawing Sheet

COMPOSITE GEL-FOAM AIR FRESHENER

BACKGROUND OF THE INVENTION

Gel-based air freshener products have been formulated from (i) an aqueous medium containing a volatile air freshener (odorizer or deodorizer) component, and (ii) an agent which gels the aqueous medium. In operation, the volatile air freshener components are continuously released from the gel by room temperature evaporation of the aqueous medium within the gel. Volatile air freshener components can include volatile oils which provide a pleasant odor and/or mask unpleasant odors, as well as disinfectants, bactericides and insecticides.

The formulations of many gel-based air fresheners utilize carrageenan as a gelling agent. For example, British Patent Specification No. 1,241,914 (published Aug. 4, 1971) discloses a biocidal and/or deodorizing composition which includes 1–6 percent of a gelling agent, and 99–94 percent of an aqueous medium containing the active biocidal and/or deodorizing agents, which in turn represent 1–10 percent of the gel. The gelling agent is a mixture of the kappa and iota fractions of carrageenan, in ratio of 1.5:1–7:1, respectively.

M. Lanzet (U.S. Pat. No. 2,927,055, issued Mar. 1, 1960) discloses an air treating gel composition which consists essentially of 97–98 percent of an aqueous medium, of which 1–10 percent are "air treating components" including a mixture of essential oils, and about 2–3 percent of an aqueous gelling agent. In terms of weight percentage of the complete gel formulation, the aqueous gelling agent is formed from 0.75–1.8 percent carrageenan, 0.2–0.75 percent locust bean gum, 0.1–0.75 percent potassium chloride, and 0.15–0.7 percent sodium carboxymethyl-cellulose.

Lin (U.S. Pat. No. 4,056,612, issued Nov. 1, 1977) discloses an air freshener gel consisting essentially of about 1.5–4 percent of a gelling agent, and 98.5–96 percent of an aqueous medium containing a volatile air freshener component. The three-component gelling agent contains at least 40 percent carrageenan, 0.6–2 percent kappa carrageenan, 0.2–1 percent locust bean gum, and 0.05–1 percent of a water soluble ammonium salt having a pH greater than 5.0. The disclosed compositions may also contain co-solvents, such as ethanol, isopropanol, ethylene glycol, propylene glycol, hexalin glycol, or cellosolve; bactericides or fungicides; dyes; or emulsifiers.

A recurring problem with the solid air freshener compositions based primarily on carrageenan as the gelling agent is syneresis, i.e., the loss of moisture from the gel to the surface, thus giving the gel a wet appearance. More specifically, syneresis results in a separation of the aqueous medium from the gel, due to gel contraction and/or inadequate water gel strength. Attempts to alleviate the syneresis problem have included incorporating various metal ions into the gels, and using carboxymethylcellulose (CMC) instead of carrageenan as the primary gelling agent.

For example, Singleton et al. (U.S. Pat. No. 3,997,480, issued Dec. 14, 1976) discloses a CMC-based gel composition, including an aqueous medium, a volatile air treating component, and a gelling agent, which consists of the reaction product of a 1–10 percent water soluble cellulose derivative, with or without modifying gums, and a metal salt having a low solubility in water. The addition of the salt to the aqueous solution of cellulose derivative is disclosed as affecting the water solubility of the cellulose derivative, so that the metal salt of the cellulose derivative is precipitated slowly and in a controlled fashion to form the gel.

Sayce et al. (U.S. Pat. No. 3,969,280, issued July 13, 1976) discloses an air freshener gel comprising water, from 0.5–10 percent of sodium or potassium CMC, 0.05–10 percent of a surfactant, 0.01–10 percent of a perfume, and a source of a trivalent metal cation selected from aluminum ions and chromic ions, in an amount sufficient to give a ratio of CMC to effective weight of trivalent cation of 1:0.01 to 1:0.1. The disclosed surfactant may be a nonionic or cationic surfactant; anionic surfactants are disclosed to be unsuitable because they interfere with the formation of gel structure. Additionally, surfactant gum-like materials, e.g., nonionic hydrocolloids, may be utilized as the surfactant. Optional ingredients can include a sequestering agent, a solvent, preservatives, dyes or colorings.

Consumer acceptance of many commercially available gel-based air freshener products has been hampered because progressive evaporation of the active substances therein can cause these products to lose their shape, or to shrink or disintegrate, eventually leaving a shapeless, shrunken and dried residue. Moreover, the reduction in surface area caused by the collapse of the gel matrix effectively reduces the rate of fragrance release; i.e., the effective fragrance-releasing surface area of these products decreases over time. Art workers have attempted to alleviate these problems by forming air fresheners from paraffin, which is a solid at room temperature, and metal soaps which gel the paraffin, such as aluminum monostearate, distearates and/or tristearates. Disadvantageously, the evaporation rate of these formulations, which affects the length of time needed to distribute the active substance within a given space and to eliminate an undesirable odor in that space, is reduced to the evaporation rate of the active substance in the product, so that it is not possible to substantially increase or decrease the rate of evaporation.

Hautmann (U.S. Pat. No. 4,117,110, Sept. 26, 1978) discloses an air improving composition which purports to address this problem by utilizing a liquid paraffin having a suitable evaporation number, in order to vary the evaporation rates of the active ingredients. The Hautmann composition comprises 5–30 percent of a carrier material consisting essentially of sodium stearate; 30–80 percent of a paraffin agent consisting of a liquid paraffin, which at 20° C., has an evaporation number ranging from 8–1000, based on an evaporation number for diethylether at 20° C. of 1; a sufficient amount of water to form a solid gel; and a deodorant agent and/or an odorant agent, or a mixture thereof.

Another disadvantage of known gel-based air freshener systems is temperature instability. For example, carrageenan-based systems have exhibited a lack of stability when exposed to the extreme temperatures frequently encountered during storage and/or shipping in the summer and winter months. Such lack of stability is exhibited by one or more of the following: product weight loss, deterioration of product appearance, loss of effectiveness, and the like. Specifically, the poor freeze-thaw stability of such carrageenan-based compositions is shown in that samples which return to ambient from temperatures below about −20° C. exhibit a significant fluid loss, and corresponding reduction in size and appearance. Other gel compositions which utilize soaps, and more specifically stearates, as gelling agents, e.g., sodium or potassium salts of stearic acid, also exhibit poor temperature stability, especially at high temperatures. For example, samples which are returned to ambient temperatures after having been exposed to temperatures of above about 48° C. lose their integrity completely, and liquify.

In an attempt to solve the problems of high- and low-temperature stability, Streit et al. (U.S. Pat. No. 4,178,264, Dec. 11, 1979) utilized a blend of carrageenan and stearate salt as a gelling agent. The air treating gels disclosed by Streit et al. comprise 1.5-15 percent of a 0.3:1 to 5:1 weight ratio of carrageenan and stearate salt; from 0.5-6 percent of essential oils and aromatics, from 1.0-20.0 percent of a solvent component; and the balance water. Suitable stearates may include sodium and potassium stearates as well as alkanolamines. The solvent component may include glycols such as ethylene glycol, liquid polyethylene glycols having a molecular weight from about 200-600, solid polyethylene glycols having an average molecular weight from about 1000-7500, ethylene and polyethylene glycol monomethyl ethers, and $C_2$-$C_{18}$ alcohols.

British Patent Specification No. 1,598,449 (published Sept. 23, 1981) discloses air-freshening gels which are stearate-based, or "soap"-gels, in contrast with water-based gels. The disclosed soap-gels form a substantially rigid composition which contains: (1) a soap, such as sodium stearate; (2) an alcoholic medium comprising a monoalkyl ether of an alkaline glycol; and (3) one or more volatile air treating components.

In addition to gel-based compositions, plastic foam-based structures have also been utilized as air fresheners. For example, "in-situ" impregnation of polyurethane foams has been accomplished by adding ingredients such as room deodorizers to the foam reactant phase during the production or foaming process. However, polyurethane foam systems formed by "in situ" techniques are disadvantageous in that the amount of active ingredients that can be added to the initial foam reactant mix is limited. Additionally, many polyurethane foaming systems involve exothermic reactions which may generate excess heat or cause adverse chemical reactions to occur. Such reactions may be especially harmful to heat-sensitive fragrances.

Palinczar et al. (U.S. Pat. No. 4,339,550, issued July 13, 1982) discloses a hydrophilic foam impregnated with volatile organic ingredients. The composition may be formed "in-situ" by reacting 5-85% of a capped polyoxyethylene polyol prepolymer with 5-75% of water and 0.1-25% of the volatile organic ingredient. From 1-40% of a surface active agent, and 5-80% of a "control release ingredient" intended to control the release rate of the volatile component, may also be included in the foam. The "control release" ingredient may include, e.g., gums such as hydroxypropylmethylcellulose, sodium carboxymethylcellulose and karaya gum.

Commonly-assigned U.S. Pat. No. 4,581,385 to Smith et al. discloses the preparation of foams useful as carpet cleaning compositions. The foams are formed by foaming a polyurethane prepolymer resin with an aqueous reactant phase comprising a slurry of solid abrasive particles and a surfactant. The disclosed reactant phase may optionally contain a minor amount of a volatile odoriferous agent which is chemically compatible with the surfactant, in order to deodorize carpet and freshen room air. The foam is cured to form a bun having a tensile strength of less than about 10 p.s.i., which is subsequently shredded to form foam particles having a size of about 5-20 mesh.

As mentioned above, difficulties have been encountered in attempts to control the release rate of volatile air freshener ingredients. For example, commercially available solid (gel- or paraffin-based) air fresheners are "first-order" systems; i.e., characterized by a "first-order" evaporation rate of their volatile components. In first-order evaporation, evaporation is initially high, but rapidly levels off to an ineffective amount. Thus, consumers who use the solid products have found that they are too strong at first, but quickly become barely noticeable.

In contrast to the solid systems, liquid air freshener products are known which may achieve the desired "zero-order" release rate. These products utilize a wick device to gradually draw up a fragrant liquid from a reservoir, and thus may steadily release the fragrance as long as the liquid lasts. Disadvantageously, these liquid systems utilize large amounts of the active ingredients in a short amount of time, and are thus correspondingly more expensive. Further, ease of use is less with liquid products than with solid products, because the liquid ingredients may easily be spilled. If spilled, the liquid ingredients may damage the surface on which the product was placed.

Therefore, a need exists for an air freshener product which is long-lasting, convenient to use, and which can achieve a sustained release rate of the volatile air freshening ingredients therein.

SUMMARY OF THE INVENTION

The present invention provides a solid air freshening article having a composite structure which incorporates a gelled phase and a granular foam phase. Both the gelled phase and the granular foam phase can include a defined amount of a volatile air freshening ingredient. The foam granules are dispersed throughout the gelled phase in a weight ratio of about 1:2-20 so as to provide for the sustained release of an effective amount of the volatile air freshening ingredient from the composite air freshening article. As used herein, "effective amount" of the volatile air freshening ingredient refers to an amount sufficient to scent, permeate, or otherwise odorize a standard-sized room in a typical residential dwelling. The use of the term "solid" with respect to the present air fresheners means that they are dimensionally stable, e.g., self-supporting. As used with respect to the granular foam phase of present fresheners, the term "dispersed throughout" means that the foam granules are distributed throughout all, or a substantial portion of the volume of the finished air freshener, e.g., at least about 50% of the total volume of the air freshener has foam particles evenly distributed throughout.

In use, the gelled phase operates as the "primary release vehicle," so that the air freshening ingredient is first released primarily from the gelled phase. As the gelled phase "shrinks" or decreases in volume over time due to evaporation or other mechanism, exposure of the dispersed foam granules to the ambient environment increases. These foam granules can also incorporate the air freshening ingredient. Increased exposure of the foam granules represents an increase in the surface area from which the air freshening ingredient can be released, i.e., the "effective fragrance-releasing surface area" of the composite article can increase over time. In this manner, the granular foam phase gradually takes over as the "secondary release vehicle" for the volatile air freshening ingredient, providing for its sustained release. This effect is in marked contrast to prior art systems which exhibit decreasing fragrance-releasing surface areas, and thus, rapidly decreasing fragrance intensities, over time.

In a preferred embodiment, the overall rate of release of the volatile air freshening ingredient from the composite air freshening article is a substantially zero-order rate of release. As used herein, the phrase "substantially zero order" means that the rate of release, e.g., by evaporation, of the volatile air freshening ingredient is substantially constant or steady-state over the useful life of the composite air freshening article. "Overall" rate of release refers to the total rate of release of the volatile air freshening ingredient(s) from the composite article, which release may be contributed to by release from the gelled phase, release from the granular foam phase, or simultaneous release from both phases. "Useful life" refers to the period of time in which an effective portion of the air freshening ingredient remains to be evaporated or otherwise released from either phase of the composite air freshener.

Therefore, the present invention provides a solid composite air freshening article comprising (a) a gelled phase, and (b) a granular foam phase, wherein both phases including a defined amount of one or more volatile air freshening ingredients. The granular foam phase is dispersed throughout the gelled phase so as to provide for the sustained release of an effective amount of the volatile air freshening ingredients. The volatile air freshening ingredient present in the gelled phase is preferably, although need not be, the same as the volatile air freshening ingredient in the granular foam phase. Preferably, the air freshening article comprises about 70-95% by weight of the gelled phase, and about 5-30% of the granular foam phase.

In addition to the volatile air freshening ingredient, the gelled phase preferably comprises an organic solvent, water, and an effective amount of a gelling agent. The gelled phase can further comprise a nonionic surfactant, as well as minor amounts of adjuvants such as a dye or preservative. The granular foam phase preferably comprises a plurality of granules of a hydrophilic, polyurethane foam which incorporate a volatile air freshening ingredient, a surfactant and a solid filler material. The foam has a network of interconnected, substantially open cells, the walls of which incorporate both the solid filler material and an aqueous phase that comprises the volatile air freshening ingredient and the surfactant. The foam is formed by foaming a prepolymer resin with an aqueous foam reactant phase. This aqueous phase can also include a solvent, a silane-coupling agent, and a silicone fluid, as well as minor amounts of adjuvants such as a dye or preservative, which become incorporated into the cured foam.

The present invention also provides a method for forming a solid composite air freshening article. The method comprises the steps of (a) forming a gel reactant phase which comprises water, an organic solvent, a first volatile air freshening ingredient, and an effective amount of a gelling agent; (b) forming an aqueous foam reactant phase which comprises water, a surfactant, a solid filler material, and a second volatile air freshening ingredient; (c) mixing the aqueous foam reactant phase with a water-foamable prepolymer resin that contains at least 2 free isocyanate groups per resin molecule, so that the final mole ratio of water to total free isocyanate groups is within the range of about 5-100:1, thus converting the resin into a hydrophilic polyurethane foam bun; (d) shredding the foam bun to form foam granules having a granule size about 5-20 mesh; (e) contacting about 5-30% of the plurality of foam granules with about 70-95% of the gel reactant phase, so as to form a gellable composite article; and (f) gelling the gellable composite article to yield a substantially solid form.

The present invention also encompasses a method for providing a sustained release of one or more volatile air freshening ingredients. The method comprises the steps of (a) providing a composite air freshening article comprising (i) a gelled phase formed from a mixture of ingredients comprising a first volatile air freshening ingredient, and (ii) a granular foam phase incorporating a second volatile air freshening ingredient, wherein the granular foam phase is dispersed throughout the gelled phase; (b) evaporating the first volatile air freshening ingredient from the gelled phase over time, so as to increase an exposed surface area of the granular foam phase as the gel phase is consumed; and (c) contemporaneously with or after initiation of step (b), evaporating the second volatile air freshening ingredient from the granular foam phase. In preferred applications of the method, the first volatile air freshening ingredient is the same as the second volatile air freshening ingredient.

All percentages of ingredients or phases given herein are weight percentages of the entire air freshening article, unless otherwise indicated.

DETAILED DESCRIPTION OF THE INVENTION

A. Effective Fragrance-Releasing Surface Area

Figure 1A:
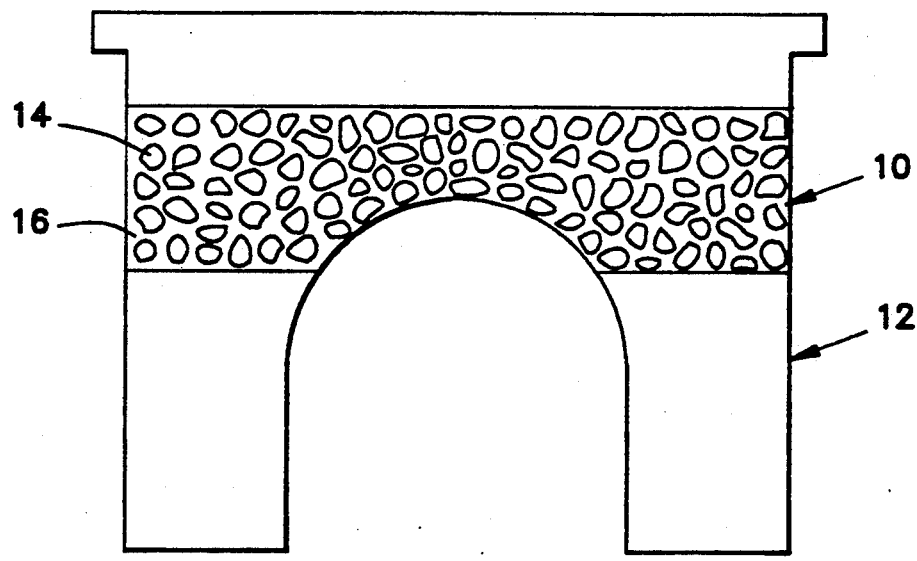
FIGS. 1A and 1B are schematic illustrations of one embodiment of the invention, which illustrate the manner in which the effective fragrance-releasing surface area of the present gel-foam composite air freshening article increases over time.
Figure 1B:
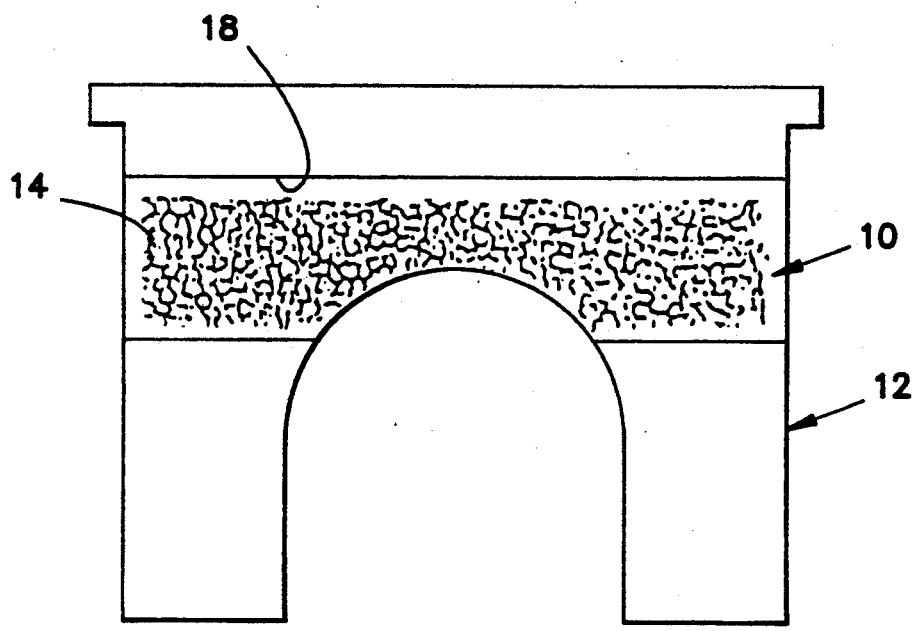

The present solid composite air freshening article comprises a granular foam phase dispersed throughout a gelled phase. This unique multi-phase structure provides for an increase in the article's effective fragrance-releasing surface area over time. This effect is depicted in FIGS. 1A and 1B, which illustrate the composite article mounted in a cassette. This arrangement is particularly useful when the present air freshening article is to be utilized in conjunction with a mechanically-driven fan unit.

More specifically, FIG. 1A depicts a cross-sectional view of the air freshening article, referred to generally by reference numeral 10, as it is positioned within cassette 12. A plurality of exposed foam granules 14 are shown dispersed throughout gelled phase 16. At the initial state depicted in FIG. 1A, the gelled phase 16 is the primary fragrance release vehicle.

FIG. 1B depicts a cross-sectional view of article 10 after the fan unit has been in operation for a prolonged period, e.g., several weeks. The overall dimensions of article 10 are somewhat reduced in comparison to those shown in FIG. 1A, due to the "shrinking," evaporation, syneresis or other loss mechanism operating on gelled phase 16 (not shown in FIG. 1B). As depicted by reference numeral 18, a portion of the interior volume of cassette 12 which was previously filled by article 10 is now vacant.

Although the overall dimensions of the air freshening article 10 have decreased, as shown in FIG. 1B the shrinking of the gelled phase has resulted in a marked increase in the exposed surface area of the foam granules 14. Many of the exposed granules 14 shown in FIG. 1B were previously covered by the gelled phase 16, as shown in FIG. 1A. The increase in number of exposed foam granules 14 over time represents an increase in the effective fragrance-releasing surface area of the present composite air freshening article over time, which provides for the sustained release of the volatile air freshening ingredients therein during the useful life of the air freshener.

B. Granular Foam Phase

The foam granules of the present invention are prepared by a process which comprises forming an aqueous slurry that includes a volatile air freshening ingredient and particles of a solid filler material. The slurry or "aqueous foam reactant phase" further includes an amount of surfactant effect to form an open-celled foam upon reaction of the aqueous phase with a water-foamable polyurethane prepolymer resin. In the practice of the present invention, nonionic and anionic surfactants are preferred. The aqueous phase may further comprise additional foam-forming and structuring agents such as silicone fluids, additional surfactants, organic solvents and the like which can affect the structure of the foam. Minor but effective amounts of adjuvants such as dyes and preservatives may also be included in the aqueous phase. The fully-formed aqueous phase is then combined with a water-foamable prepolymer resin, and the reaction mixture allowed to foam and cure to form a self-cross-linked, friable polyurethane bun. The bun is chopped or shredded into particulate foam granules which constitute the granular foam phase of the present invention. As used herein, the term "bun" is intended to refer generally to the foam body which is the precursor of the shredded foam granules, and can include slab stock sheets as well as molded bodies.

1. Prepolymer Resins

A commercially available class of water-foamable prepolymer resins which yield cross-linked, hydrophilic polyurethane foams upon the addition of stoichiometric excesses of water are those belonging to the Hypol® series (W. R. Grace & Co.; FHP 3000, 2000, 2000 HD, 2002) which are generally described in U.S. Pat. No. 4,137,200, the disclosure of which is incorporated by reference herein. These liquid resins are prepared by capping mixtures of low molecular weight polyols having 3-8 hydroxyl groups and polyoxyethylene diols with toluene diisocyanate. The capped alcohol mixtures have an average number of free isocyanate groups per molecule which is equal to two or more, i.e. 2-8.

These resins possess molecular weights within the range of about 1300-1400 and have about 1.5-2.5 mEq/g of free isocyanate groups. Upon being contacted with a molar excess of water, the isocyanate groups hydrolyze to release carbon dioxide gas, thus foaming the resin without the need for added catalysts or blowing agents. The free amino groups formed by the hydrolysis reaction react with unhydrolyzed isocyanate groups to form ureido groups which cross link and stabilize the foam, while entrapping a part of the excess aqueous phase in the cell walls, where it acts to impart hydrophilic properties to the foam.

Other poly-$C_2$-$C_3$-alkyleneoxy glycols capped with aromatic isocyanates may be prepared which possess a suitable balance between their extent of cross-linking prior to foaming and their ability to cross-link or to further cross-link during foaming (due to the presence of more than two reactive isocyanate groups per resin molecule), so as to be useful in the practice of the present invention over the entire range of solids and surfactant content. These prepolymer resins are prepared by polymerizing ethylene oxide to yield polyalkylenoxy polyols having a molecular weight of about 900-1100. These polyols are reacted with a stoichiometric excess of a polyisocyanate. Suitable isocyanates include toluene diisocyanate, triphenylmethane-4,4',4''-triisocyanate, benzene-1,3,5-triisocyanate, hexamethylene diisocyanate, xylene diisocyanate, chlorophenylene diisocyanate and mixtures thereof. The useful resins recovered have a somewhat lower number of mEq of free isocyanate groups (NCO) per gram of resin than do the Hypol® resins, e.g. 1.3-1.5 mEq/gram and exhibit a substantially higher tensile strength when foamed and cured at ambient temperatures to incorporate high percentages of dispersed abrasives.

Commercially available self cross-linking resins include Trepol® A-62 and TRE STD ®prepolymer resin (Twin Rivers Engineering Co., East Booth Bay, ME), which form acceptable foams upon reaction with at least a stoichiometric excess of water without employing a low molecular weight polyol component to raise the average number of free isocyanate groups per glycol ether molecule to above two. TRE STD ® resin has an average free isocyanate content of about 1.4 mEq/gram, comprises a polyol component having an average molecular weight of about 1000, exhibits a viscosity at 32° C. of 4700 cps and solidifies at 15.5° C.

In the practice of the present invention, useful foams may be formed employing a weight ratio of water to prepolymer resin of 0.5-2.5:1, preferably 0.75-2.0:1. These ranges yield a mole ratio of water to free isocyanate groups of about 20-80:1, preferably about 30-60:1.

2. Solid Filler Material

Particulate solids can be employed as filler material in the present foam granules, and are dispersed throughout the foam matrix. The filler material adds volume to the foam matrix, but is typically not an active ingredient. The choice of filler material may be made from a wide variety of materials of hardness and particle size range.

Useful filler materials include minerals such as aluminates and silicates, including alumina, silica, feldspars, zeolites, clays, carborundum, zircon, clays, quartz and the like. When used, the solids will preferably comprise about 30-70% by weight of the aqueous reactant phase, most preferably about 40-60%. The weight ratio of solid filler to prepolymer which may be used is limited only by the ability of the foamed polymeric matrix to retain the particles without undue separation and loss of the solid during preparation or shipping. Preferably, the weight of the solid filler material used will be from about 100-500% of the prepolymer weight, most preferably 150-300%. These high weight ratios of solids to prepolymer resin yield dense foam buns and shreds which can incorporate about 55-75% of the solid filler material on a total-foam dry weight basis. The air freshener can also include minor amounts of other solids which are separately present in either the gelled phase or the foam phase, e.g., solids which may be present in the surfactant and/or the silicone fluid components of the foam phase.

A preferred filler material for use in the foams of the present invention is NC-4 Feldspar ® (170 or 200 mesh) available from Feldspar Corp. of America, Spruce Pine, N.C.

3. Organic Solvents

The aqueous reactant phase also preferably includes a water-soluble or water-dispersible organic solvent or solvent mixture, which acts to help dissolve or disperse water-insoluble components such as silicone oils and fragrance oils in the aqueous phase. Solvents may be selected from hydrocarbons, alcohols, ethers or esters, such as isoparaffins, m-pyrol, tetrahydrofurfuryl alcohol (THFA), butyl carbitol, alkyl cellusolves, mineral spirits, propylene glycol ethers, propylene glycol ether acetates (Arcosolvs ®) and the like. These solvents may be used in effective amounts of up to about 15%, preferably about 6-12% by weight of the aqueous phase. Preferred solvents include the isoparaffinic solvents available as ISOPAR ® K and ISOPAR ® M from Exxon Co., Houston, Tex.

4. Surfactants

One or more foam-structuring surfactants will also be incorporated into the aqueous phase. The foam-structuring surfactants are preferably selected from nonionic and/or anionic types which are soluble or dispersible in water.

Preferred nonionic surfactants include the condensation products of ethylene oxide with a hydrophobic polyoxyalkylene base formed by the condensation of propylene oxide with propylene glycol. The hydrophobic portion of these compounds has a molecular weight sufficiently high so as to render it water insoluble. The addition of polyoxyethylene moieties to this hydrophobic portion increases the water solubility of the molecule as a whole, and the liquid character of the product is retained up to the point where the polyoxyethylene content is about 50% of the total weight of the condensation product. Examples of compounds of this type include certain of the commercially available Pluronic ® surfactants (BASF Wyandotte Corp.), especially those in which the polyoxypropylene ether has a molecular weight of about 1500-3000 and the polyoxyethylene content is about 35-55% of the molecule by weight, i.e. Pluronic ® L-62. Other useful nonionic surfactants include the condensation products of $C_8$–$C_{22}$ alkyl alcohols with 2-50 moles of ethylene oxide per mole of alcohol. Examples of compounds of this type include the condensation products of $C_{11}$–$C_{15}$ secondary alkyl alcohols with 3-50 moles of ethylene oxide per mole of alcohol which are commercially available as the Poly-Tergent ® SLF series from Olin Chemicals or the Tergitol ® series from Union Carbide, i.e. Tergitol ® 25-L-7, which is formed by condensing about 7 moles of ethylene oxide with a $C_{12}$–$C_{15}$ alkanol.

Other nonionic surfactants which may be employed include the ethylene oxide esters of $C_6$–$C_{12}$ alkyl phenols such as (nonylphenoxy)polyoxyethylene ether. Particularly useful are the esters prepared by condensing about 8-12 moles of ethylene oxide with nonylphenol, i.e. the Igepal ® CO series (GAF Corp., New York, N.Y.).

Other useful nonionics include the ethylene oxide esters of alkyl mercaptans such as dodecylmercaptan polyoxyethylene thioether, the ethylene oxide esters of fatty acids such as the lauric ester of polyethylene glycol and the lauric ester of methoxypolyethylene glycol, the ethylene oxide ethers of fatty acid amides, the condensation products of ethylene oxide with partial fatty acid esters of sorbitol such as the lauric ester of sorbitan polyethylene glycol either, and other similar materials, wherein the mole ratio of ethylene oxide to the acid, phenol, amide or alcohol is about 0.5-50:1.

Useful anionic surfactants include the alkali metal salts of sulfated ethylenoxy fatty alcohols (the sodium or ammonium sulfates of the condensation products of about 1-4 moles of ethylene oxide with a $C_{12}$-$C_{15}$ n-alkanol, i.e., the Neodol ® ethoxysulfates, such as Neodol ® 25-3S, Shell Chemical Co.); anionic detergent salts having alkyl substituents of 8 to 22 carbon atoms such as the water-soluble higher fatty acid alkali metal soaps, e.g., sodium myristate and sodium palmitate. Another useful class of anionic surfactants encompasses the water-soluble sulfated and sulfonated anionic alkali metal and alkaline earth metal detergent salts containing a hydrophobic higher alkyl moiety (typically containing from about 8 to 22 carbon atoms) such as salts of higher alkyl mono or polynuclear aryl sulfonates having from about 1 to 16 carbon atoms in the alkyl group (e.g., sodium dodecylbenzenesulfonate, magnesium tridecylbenzenesulfonate, lithium or potassium pentapropylenebenzenesulfonate). These compounds are available as the Bio-Soft ® series, i.e. Bio-Soft ® D-40 (Stephan Chemical Co., Northfield, Ill.).

Other useful classes of anionic surfactants include the alkali metal salts of sulfonsuccinic acid esters, e.g., dioctyl sodium sulfosuccinate (Monawet ® series, Mona Industries, Inc., Paterson, N.J.); the alkali metal salts of alkyl naphthalene sulfonic acids (methyl naphthalene sodium sulfonate, Petro ® AA, Petrochemical Corporation); sulfated higher fatty acid monoglycerides such as the sodium salt of the sulfated monoglyceride of coconut oil fatty acids and the potassium salt of the sulfated monollyceride of tallow fatty acids; alkali metal salts of sulfated fatty alcohols containing from about 10 to 18 carbon atoms (e.g., sodium lauryl sulfate and sodium stearyl sulfate); sodium $C_{14}$-$C_{16}$-alpha-olefin sulfonates such as the Bio-Terge ® series (Stephan Chemical Co.); alkali metal salts of higher fatty esters of low molecular weight alkylol sulfonic acids, e.g., fatty acid esters of the sodium salt of isethionic acid; the fatty ethanolamide sulfates; the fatty acid amides of amino alkyl sulfonic acids, e.g. lauric acid amide of taurine; as well as numerous other anionic organic surface active agents such as sodium xylene sulfonate, sodium naphthalene sulfonate, sodium toluene sulfonate and mixtures thereof.

A further useful class of anionic surfactants includes the 8-(4-n-alkyl-2-cyclohexenyl)-octanoic acids wherein the cyclohexenyl ring is substituted with an additional carboxylic acid group. These compounds, or their potassium salts, are commercially available from Westvaco Corporation as Diacid ® 1550 or H-240.

In general these organic surface active agents are employed in the form of their alkali metal salts, ammonium salts or alkaline earth metal salts, as these salts possess the requisite stability, solubility, and low cost essential to practical utility.

The total amount of nonionic and/or anionic surfactant which is incorporated into the present foams is an effective amount of about 0.5-10%, preferably about 1-5% by weight of the aqueous phase.

5. Air Freshening Ingredient

The air freshening ingredients of the present invention comprise pleasant-smelling, organic, volatile aromatic compounds. Suitable materials are volatile at room temperature, compatible with each other (if mixed), and dispersable in water. Preferred air freshening ingredients include the fragrance oils commercially available from Noville, North Bergen, N.J. Other useful air freshening ingredients include the essential oils such as oil of pine, oil of lemon grass, oil of spearmint, oil of wintergreen, oil of cedarwood, oil of fir Canadian, and the like, which may be used alone or in admixture with each other or with the many aromatic esters, aldehydes, ketones and other compounds known to those skilled in the art of blending fragrances. The terms "fragrance" or "fragrances" may be used herein interchangeably with the phrases "air freshening ingredient" or "air freshening ingredients." An effective amount of up to about 12.5%, preferably about 2-10% of these air freshening ingredients will be incorporated into the aqueous phase.

6. Silicone Fluid

Silicone fluids can also be incorporated into the aqueous phase as foam cell initiating and structuring agents, and are selected from those which function to control cell size and reticulation. Useful classes of silicone fluids include the linear dimethylpolysiloxanes or the tetrameric or pentameric cyclic siloxanes (cyclomethicones) which are available from Rhone-Poulenc, Inc., Monmouth Junction, New Jersey as the Rhodorsil® 47V series, for from Dow Corning as the Dow 200 Fluid series in a wide range of viscosities; i.e., 10-10,000 cps. When used as a component of the present aqueous foam reactant phase, an effective amount of about 0.1-10%, preferably about 0.5-5% of a silicone fluid can be employed.

7. Silane Coupling Agent

The foam granules of the present invention will also include a minor but effective amount, e.g., about 0.05-2% by weight of the aqueous reactant phase, of a silane-coupling agent. These agents function by bonding to the polyurethane matrix and the surface of the particles of the solid filler material, thus chemically coupling the solid filler material into the polymeric matrix and preventing the filler particles from separating from the matrix during packaging or use. Silane-bound solid particles also clump less readily and so are more evenly dispersed throughout the solidifying matrix during the foaming reaction.

Useful silane-coupling agents may be selected from members of organosilicon monomers such as substituted-alkyl(trisalkoxy)silanes which can be characterized by the formula $RSiX_3$, wherein R is an organofunctional group attached to silicon in a hydrolytically stable manner and X designates hydrolyzable groups which are converted to silanol groups upon hydrolysis. Most commonly, R comprises a vinyl, methacryloxypropyl, 3,4-epoxycyclohexylethyl, 3-glycidoxypropyl, 3-mercaptopropropyl, 3-aminopropyl or 3-ureidopropyl moiety which may be further separated from the silicon group by one or two $-NH(CH_2)_n$ moieties wherein $n=1-2$. Preferably X is an alkoxy group selected from the group consisting of methoxy, ethoxy, 2-methoxyethoxy or is acetoxy.

Preferred silane-coupling agents are commercially available from Union Carbide as the A-series, e.g., A1100-A1160, which include 3-aminopropyltriethoxysilane, 3-aminopropyltrimethoxysilane (also available from Dow Corning as Z-6020), N-2-aminoethyl-3-aminopropyltrimethoxysilane, or 3-ureidopropyltriethoxysilane.

8. Adjuvants

Minor but effective amounts of other foam-compatible adjuvants, such as dyes, cationic or amphoteric surfactants, biocides, and the like, may be introduced into the present foam granules in effective amounts, either via the aqueous or resin phase or by treating the final product with the adjuvants as by spraying, mixing, etc. A preferred biocide is commercially available as Nuosept® 95 Preservative from Nuodex, Inc., Piscataway, N.J. When employed in the present products, such adjuvants will commonly be present at a level of up to about 0.1-5% by weight of the finished product.

9. Preferred Formulation of Granular Foam Phase

The foam granules of the present invention are formed by mixing and foaming the prepolymer resin with the aqueous reactant phase. A preferred aqueous reactant phase comprises, by weight, about 20-40%, more preferably about 25-35% water; about 35-65%, preferably about 40-55% of a particulate solid filler material; an effective amount of up to about 12.5%, preferably about 2-10% of a volatile air freshening ingredient; an effective amount of up to about 15%, preferably about 6-12% of an organic solvent; about 0.5-10%, preferably about 1-5% of a nonionic and/or anionic surfactant; about 0.1-10%, preferably 0.5-5% of a silicone fluid; about 0.05-2%, preferably about 0.1-1% of a silane coupling agent; and optionally, minor but effective amounts of dyes, biocides, and the like.

A foam matrix is formed by mixing together the aqueous phase described above with the prepolymer resin in a weight ratio of about 20-1:1, preferably about 10-2:1, and most preferably about 7.5-2.5:1. The foam granules are preferably obtained by shredding or chopping the foam matrix into granules having a mesh size of about 5-20, more preferably about 10-15, and most preferably about 12.

C. Gelled Phase

The gelled phase of the present composite article is prepared by a process which comprises gelling a mixture of ingredients that includes water, a solvent, a gelling agent, and a volatile air freshening ingredient. Although it is preferred that the air freshening ingredient present in the gel be the same as the air freshening ingredient present in the granular foam phase, this is not required; any combination of different air freshening ingredients may be employed in the present composite article. The mixture from which the gelled phase is formed may optionally further comprise a nonionic surfactant which can assist in solubilization of the organic, aromatic air freshening ingredient. If the surfactant is present, it is preferably blended together with the air freshening ingredient before adding the resulting blend to the remaining ingredients of the mixture. Minor but effective amounts of adjuvants such as dyes, preservatives, bactericides and the like may also be present in the gelled phase.

1. Gelling Agent

The mixture of ingredients from which the gelled phase is formed will comprise an effective amount of up to about 20%, preferably about 5-15% of a gelling agent. Useful gelling agents include, e.g., stearates (alkali metal salts of stearic acid), carrageenan, carboxymethyl cellulose and mixtures thereof. Gels formed by the reaction of carboxymethyl cellulose with an effective amount of chromic and/or aluminum cations may also be useful; see U.S. Pat. No. 3,969,280. Preferred stearates include the sodium stearates commercially available as Grade T-1 from Witco Chemical Corp., New York, N.Y. However, useful stearate salts can be formed in situ in the mixture of ingredients from which the gelled phase is formed, by neutralizing stearic acid with a base such as an alkali metal hydroxide, e.g., LiOH, KOH, or NaOH, which may be added to the mixture as an aqueous solution.

Sodium stearate gelling agents are particularly useful in dynamic applications of the present invention; i.e., where release of the air freshening ingredient is enhanced by a fan, air blower, or other means which artificially increases the air flow rate in the vicinity of the air freshening article. When the air freshener is used in static applications, i.e., those in which the air flow rate is not mechanically increased, carrageenan is the preferred gelling agent. However, either formulation (stearate-based or carrageenan-based), or a combination of the two, may be used in either type of application.

2. Surfactant

The gelled phase may be formed from a mixture of ingredients including an effective amount of up to about 10%, preferably about 2-6%, of a nonionic surfactant. The surfactant can assist in solubilizing the air freshening ingredient, which is preferably an aromatic, organic material as described above. Although any of the nonionic surfactants described herein as useful in the granular foam phase may also be useful as the surfactant of the gelled phase, particularly preferred nonionic surfactants are those of the Igepal ® CO series, commercially available from GAF Corp., New York, N.Y. The Igepal ® surfactants are esters prepared by condensing about 8-12 moles of ethylene oxide with nonylphenol. Igepa CO-710 is particularly preferred.

3. Air Freshening Ingredient

The mixture of ingredients from which the gelled phase is formed will include an effective amount of up to about 30%, preferably about 5-25%, of a pleasant-smelling, organic, volatile aromatic compound. Any of the air freshening ingredients mentioned hereinabove may be utilized. Preferably, the same air freshening ingredient will be utilized in both the gelled phase and the granular foam phase.

4. Solvent

The mixture of ingredients from which the gelled phase is formed will comprise a major amount, e.g., up to about 80%, preferably about 55-75% of an organic solvent. The amount of organic solvent will vary inversely with the amount of water in the gelled phase, i.e., the more water present in the gelled phase, the less organic solvent present. It is preferred that the gelled phase of the present invention contain no more than up to about 25% water, and preferably about 5-20% of water.

The gelled phase will preferably be formed by dispersing the active ingredients described above in a mixture of the water and organic solvent. More specifically, the water is added to the organic solvent and the mixture heated. The gelling agent is then slowly sifted in. When the resultant solution is clear, the fragrance and optional surfactant are added, while maintaining the solution at an elevated temperature. The resulting heated mixture will then be contacted with the granular foam phase in a mold before being allowed to gel into a solid article.

Thus, useful solvents for the gelled phase preferably comprise a water-miscible solvent or co-solvent, most preferably a glycol ether. These materials are lower(alkoxy)- or lower-(alkoxy)lower(alkoxy)-ethers of ethanol or isopropanol. Many useful glycol ethers are available under the tradenames Arcosol ® (Arco Chemical Co.) or Cellosolve ®, Carbitol ®, or Propasol ® (Union Carbide Corp.), and include, e.g., butylCarbitol ®, hexylCarbitol ®, methylCarbitol ®, and Carbitol ® itself, (2-(2-ethoxy)ethoxy)ethanol. Carbitol ® is also available in a low specific gravity formulation, Carbitol ® LG, which is especially preferred as the solvent in the present gelled phase. Carbitol ® LG has a specific gravity at 20/20° C. of 0.9890, and a viscosity at 20° C. of 4.5 cp, as compared to 1.0273 and 6.9 cp (25° C.), respectively, for Carbitol ®. The choice of glycol ether can be readily made by one of skill in the art on the basis of its volatility, water solubility, wt-% of the total dispersion, and the like. Pyrrolidinone solvents such as N-methyl-2-pyrrolidinone (M-Pyrol ®) or 2-pyrrolidone (2-Pyrol ®) can also be used, a can tetrahydrofurfuryl alcohol (THFA). Minor amounts of alkanols such as isopropanol or n-butanol can also be included.

5. Adjuvants

Minor amounts of other adjuvants, such as dyes, biocides, and the like, may be introduced into the mixture of ingredients from which the gelled phase is formed.

6. Preferred Formulation of the Gelled Phase

The gelled phase of the present invention will be formed by gelling a mixture of ingredients comprising an effective amount of up to about 20%, preferably about 5-15% of a gelling agent; an effective amount of up to about 10%, preferably about 2-6% of a nonionic surfactant; an effective amount of up to about 30%, preferably about 5-25% of an air freshening ingredient; an effective amount of up to about 80%, preferably about 55-75% of an organic solvent; an effective amount of up to about 25%, preferably 5-20% of water, and, optionally, minor but effective amounts of adjuvants such as dyes, preservatives, bactericides and the like.

The invention will be further described by reference to the following detailed examples.

EXAMPLE 1

Composite Air Freshening Article

A composite air freshening article of the present invention was prepared as described below, having the composition shown in Table 1-1.

TABLE 1-1

Composite Air Freshening Article[1]

Granular Foam Phase[2]

| Aqueous Foam Reactant Phase Ingredient: | Wt % Formulations: | | |
|---|---|---|---|
| | A-E | F-H | I |
| Water, Distilled | 28.3 | 29.0 | 29.8 |
| F-4 Feldspar, 170 Mesh | 48.0 | 49.6 | 50.1 |
| Dow 200 Fluid | 0.9 | 0.9 | 1.0 |
| A-1120 Silane | 0.2 | 0.2 | 0.3 |
| Isopar ® M | 9.0 | 9.0 | 10.0 |
| Pluronic ® L-62 | 1.6 | 1.7 | 1.7 |
| Neodol ® 25-3S | 1.8 | 1.9 | 1.9 |
| Nuosept ® 95 | 0.2 | 0.2 | 0.2 |
| Air Freshening Ingredient[3] | 10.0 | 7.5 | 5.0 |
| | 100.0 | 100.0 | 100.0 |

Gelled Phase

| Ingredient | Wt % (All Formulations) |
|---|---|
| Carbitol ® LG | 66.0 |
| Water, Distilled | 12.0 |
| Sodium Stearate T-1 | 8.0 |
| Igepal ® CO-710 | 4.0 |
| Air Freshening Ingredient[4] | 10.0 |
| | 100.0 |

[1] Ratio of granular foam phase:gelled phase was 15:85 (w/w) in all formulations A-I.
[2] Ratio of aqueous phase:pre-polymer resin (Hypol 3000) was 83:17, in all formulations A-I.
[3] The air freshening ingredient used in each of formulations A-I was as follows:
(A) Noville Citrus #29 Oil (S/N #32232)
(B) Noville Citrus #3 Oil (#32062)
(C) Noville Powder #7 Oil (#28019)
(D) Noville Fruity Floral #32 Oil (#32237)
(E) Noville Herbal Floral #8 Oil (#29513)
(F) Noville Powder #34 Oil (#32245)
(G) Noville Fruity Floral #35 Oil (#24815)
(H) Noville Herbal Floral #40 Oil (#28551)
(I) Noville Herbal Floral #20 Oil (#32067)
[4] The fragrance used for each gelled phase formulation was the same as that used in the corresponding granular foam phase formulation.

A granular foam phase having formulation A (Table 1-1) was prepared as follows: A mixing vessel was charged with 627.8 g of distilled water heated to 25° C. 1065.8 g of 170 mesh F-4 Feldspar powder were sifted into the water, with agitation, followed by the addition of 5.4 g of an aminosilane ester coupling agent, Union Carbide A-1120. Agitation was continued for 30 minutes, after which time 36.2 g Pluronic ® L-62 nonionic surfactant were added. After 5 more minutes of mixing, 40.0 g of Neodol ® 25-3S were added, with 15 more minutes of mixing. Then 20.0 g of silicone fluid, Dow 200, were added, and the resultant mixture agitated for 5 more minutes. Isopar ® M solvent (200.0 g) was next added, and the resultant mixture agitated for 10 more minutes. Then 4.8 g of Nuosept ® 95 preservative were added, with agitation for an additional 15 minutes. 149.4 g of the resultant mixture were then mixed with 16.6 g of a volatile air freshening ingredient, Noville Citrus # 29 Oil (S/N #32232).

After two minutes of vigorous stirring, a 166.0 g portion of the resultant aqueous reactant phase was cooled to a temperature of 25° C. To this mixture were added 34.0 g of pre-polymer resin, Hypol ® 3000, which had been warmed to 35° C. The resultant foaming mixture was immediately poured into a 9 cm I.D. x 14 cm cylindrical, polyethylene-lined mold, and allowed to rise and cure.

After about two hours of curing, the resultant solid foam "bun" was fed into a rotary blade shredder to form foam granules of various sizes. The granules were then screened through a series of sieves in order to collect granules having a mesh size of 12. Six grams of the 12 mesh granules were uniformly distributed in the bottom of a 9.5 cm O.D. circular mold.

The gelled phase was then prepared as follows:

A beaker was charged with 1320 g Carbitol ® LG solvent and 240 g distilled water, and the resultant mixture heated to 80° C. with agitation. A gelling agent (160 g of sodium stearate T-1) was then slowly sifted in, while maintaining the temperature at 80° C. When the solution was clear and free of particles, 80.0 g of Igepal ® CO-710 surfactant and 200.0 g of Noville citrus # 29 oil (S/N #32232) were added, as a blend, to the solution. The temperature was maintained at 80° C. for an additional five minutes of mixing.

The resultant mixture (34.0 g) was poured at 80° C. into the mold containing the foam granules, so as to uniformly cover the granules. The depth of the mixture in the mold was about 1.6 cm. In order to gel the mixture, the mold was covered with aluminum foil and allowed to set for 24 hours. The resulting composite air freshener was an upright, free-standing article having the shape of the mold in which it had been gelled.

Four samples of each of formulations A through I were prepared in similar fashion, according to the formulations shown in Table 1-1. Each finished composite air freshening article weighed about 40 g.

EXAMPLE 2.

Fragrance Intensity Study

The time-course of the intensity of the fragrance released by a composite air freshening article prepared according to Example 1, Formulation F (air freshening ingredient: Noville Powder # 34 Oil (S/N 32245)), was compared to that of a commercial liquid-based air freshener, Magic Mushroom ® (powder fragrance), available from Airwick Industries, Inc., Wayne, N.J., as follows:

The 40 g composite article of Example 1, Formulation F was placed in the center of a closed box of dimensions 3 ft X 3 ft by 3 ft, having a hinged lid which could be lifted to facilitate smelling of the box interior by consumers. The Magic Mushroom ® product was placed in an identical box. A panel of consumers was asked to smell each of the two air fresheners by lifting the hinged lid, and to state which air freshener emitted the more intense fragrance. The panel studies were conducted as "blind" studies; i.e., the panel members were not told the source or identity of, or any other information regarding either air freshener.

A total of six such consumer panel studies were performed over successive weeks. Each consumer panel was made up of individuals who had not been part of a prior panel. In between each panel study, the composite air freshener was installed in a commercial fan unit, i.e., the SeBreeze ™ Automatic Odor Control System available from Rubbermaid ® Commercial Products Inc., Winchester, Va., which circulated air around the composite air freshener.

The consumer testing results are tabulated in Table 2-1 below:

TABLE 2-1

| | Fragrance Intensity Comparison | | | | | |
|---|---|---|---|---|---|---|
| | Number of Panelists | | | | | |
| Week: | #0 | #1 | #2 | #3 | #4 | #5 |
| Composite Gel-Foam Air Freshening Article of Example 1, | 18 | 17 | 15 | 18 | 18 | 12 |

TABLE 2-1-continued

| | Fragrance Intensity Comparison | | | | | |
|---|---|---|---|---|---|---|
| | Number of Panelists | | | | | |
| Week: | #0 | #1 | #2 | #3 | #4 | #5 |
| Formulation F Magic Mushroom ® (Powder Fragrance), Airwick Industries | 4 | 1 | 0 | 0 | 0 | 0 |

These results indicate that the fragrance release from the present gel-foam air freshening article was substantially longer-lasting and more intense than the fragrance release from a representative commercially available air freshener.

The invention has been described with reference to various specific and preferred embodiments and techniques. However, it should be understood that many variations and modifications may be made while remaining within the spirit and scope of the invention.

We claim:

1. A solid composite air freshening article comprising:
   (a) a gelled phase, comprising up to about 25% water, about 55-80% of an organic solvent, an effective amount of up to about 30% of a first volatile air freshening ingredient, and an effective amount of up to about 20% of a gelling agent; and
   (b) a granular foam phase, comprising about 5-20 mesh granules of a hydrophilic polyurethane foam incorporating a second volatile air freshening ingredient, a foam-structuring surfactant and a solid filler material;
   wherein said granular foam phase is dispersed throughout said gelled phase in a weight ratio of about 1:2-20 so as to provide for the sustained release of an effective air-freshening amount of said volatile air freshening ingredients from said article.

2. The air freshening article of claim 1 wherein said first volatile air freshening ingredient is the same as said second volatile air freshening ingredient.

3. The air freshening article of claim 1 comprising about 70-95% of said gelled phase.

4. The air freshening article of claim 1 comprising about 5-30% of said granular foam phase.

5. The air freshening article of claim 1, wherein said gelled phase comprises about 55-75% of said organic solvent, about 5-15% of said gelling agent, about 5-25% of said first volatile air freshening ingredient, and the balance water.

6. The air freshening article of claim 1, wherein said gelling agent is selected from the group consisting of alkali metal stearates, carrageenan, carboxymethyl cellulose and mixtures thereof.

7. The air freshening article of claim 1, wherein either of said first or second volatile air freshening ingredients comprises one or more essential oils.

8. The air freshening article of claim 1, wherein said gelled phase further comprises about 2-6% of a nonionic surfactant.

9. The air freshening article of claim 1, wherein said gelled phase further comprises a minor amount of a dye or preservative.

10. The air freshening article of claim 1, wherein said hydrophilic, polyurethane foam is substantially open celled.

11. The air freshening article of claim 10, wherein walls of said substantially open cells incorporate said solid filler material and an aqueous phase which comprises said volatile air freshening ingredient and said surfactant.

12. The air freshening article of claim 11, wherein said aqueous phase comprises about 2-10% of said second volatile air freshening ingredient.

13. The composite air freshening article of claim 11, wherein said aqueous phase comprises about 0.5-10% of said surfactant.

14. The composite air freshening article of claim 13, wherein said surfactant is selected from the group consisting of an anionic surfactant, a nonionic surfactant, and mixtures thereof.

15. The composite air freshening article of claim 11, wherein said aqueous phase further comprises about 6-12% of a solvent.

16. The composite air freshening article of claim 11, wherein said aqueous phase further comprises about 0.05-2% of a silane-coupling agent.

17. The composite air freshening article of claim 11, wherein said aqueous phase comprises about 0.1-10% of a silicone fluid.

18. The composite air freshening article of claim 11, wherein said aqueous phase further comprises a minor amount of a dye or preservative.

19. The air freshening article of claim 1, wherein said solid filler material is selected from the group consisting of alumina, silica, feldspars, zeolites, clays, carborundum, zircon, quartz, and mixtures thereof.

20. The composite air freshening article of claim 1 wherein the granular foam phase comprises about 55-75% of said solid filler material on a total-foam dry weight basis.

21. The composite air freshening article of claim 1, wherein said foam granules have granule size of about 10-15 mesh.

22. A method for forming a solid composite air freshening article comprising the steps of:
   (a) forming a gel reactant phase comprising up to about 25% of water, an effective amount of up to about 20% of a gelling agent, about 55-80% of an organic solvent, and an effective amount of up to about 30% of a first volatile air freshening ingredient;
   (b) forming an aqueous foam reactant phase comprising about 20-40% water, about 0.5-10% of a foam-structuring surfactant, about 30-70% of a solid filler material, and an effective amount of up to about 12.5% of a second volatile air freshening ingredient;
   (c) mixing said aqueous foam reactant phase with a water-foamable prepolymer resin which contains at least 2 free isocyanate groups per resin molecule so that the final mole ratio of water to total free isocyanate groups is within the range of about 5-100:1, so as to convert said resin into a hydrophilic polyurethane foam bun;
   (d) shredding said foam bun to form foam granules having a granule size about 5-20 mesh;
   (e) contacting about 5-30% of foam granules with about 70-95% of said gel reactant phase, so as to form a gellable composite article; and
   (f) gelling said gellable composite article to yield a substantially solid article.

23. A composite air freshening article formed from a process comprising the steps of:
   (a) forming a gel reactant phase comprising about 5-15% of a gelling agent; about 55-75% of a solvent; about 5-25% of a first volatile air freshening ingredient; about 2-6% of a nonionic surfactant, and the balance water;

(b) forming an aqueous foam reactant phase comprising about 30-70% solid filler, about 2-10% of a second volatile air freshening ingredient; about 6-12% of a solvent; about 0.5-10% of a surfactant; and the balance water;

(c) mixing said aqueous foam reactant phase with a water-foamable prepolymer resin which contains at least 2 free isocyanate groups per resin molecule so that the final mole ratio of water to total free isocyanate groups is within the range of about 5-100:1, so as to convert said resin into a hydrophilic polyurethane foam bun;

(d) shredding said foam bun to form foam granules having a granule size about 5-20 mesh;

(e) contacting about 70-30% of said gel reactant phase with about 5-30% of said foam granules arranged within a mold, so as to form a gellable composite article; and (f) gelling said gellable composite article to yield a substantially solid article.

24. A method for providing a sustained release of one or more volatile air freshening ingredients, said method comprising the steps of:

(a) providing a composite air freshening article comprising (i) a gelled phase, comprising up to about 25% water, about 55-80% of an organic solvent, an effective amount of up to about 30% of a first volatile air freshening ingredient, and an effective amount of up to about 20% of a gelling agent; and (ii) a granular foam phase, comprising about 5-20 mesh granules of a hydrophilic, polyurethane foam incorporating a second volatile air freshening ingredient, a foam-structuring surfactant and a solid filler material; wherein said granular foam phase is dispersed throughout said gelled phase in a weight ratio of about 1:2-20 so as to provide for the sustained release of an effective air-freshening amount of said volatile air freshening ingredients from said article;

(b) evaporating said first volatile air freshening ingredient from said gelled phase over time, so as to increase an exposed surface area of said granular foam phase as said gel phase is consumed; and (c) contemporaneously with or after initiation of said step (b), evaporating said second volatile air freshening ingredient from said granular foam phase.

* * * * *

UNITED STATES PATENT AND TRADEMARK OFFICE
CERTIFICATE OF CORRECTION

PATENT NO. : 5,034,222
DATED : July 23, 1991
INVENTOR(S) : Kellett et al.

It is certified that error appears in the above-identified patent and that said Letters Patent is hereby corrected as shown below:

Column 13, line 46, for "Igepa CO-710" read --Igepal® CO-710--.

Column 14, line 18, for "Arcosol®" read --Arcosolv®--.

Column 19, line 21, for "70-30%" read --70-95%--.

Signed and Sealed this

Twenty-second Day of December, 1992

Attest:

DOUGLAS B. COMER

*Attesting Officer*  *Acting Commissioner of Patents and Trademarks*